US005133938A

United States Patent [19]

Glanville et al.

[11] Patent Number: 5,133,938

[45] Date of Patent: Jul. 28, 1992

[54] LOCKABLE VALVE MECHANISM FOR SAMPLE POUCH

[75] Inventors: Thomas W. Glanville, Churchville; Mark J. Devaney, Jr., Rochester, both of N.Y.

[73] Assignee: Eastman Kodak Company, Rochester, N.Y.

[21] Appl. No.: 603,588

[22] Filed: Oct. 25, 1990

[51] Int. Cl.[5] .......... B01L 1/00; B01L 9/00; F16K 1/00; A61M 39/00

[52] U.S. Cl. .......... 422/102; 422/103; 422/104; 422/100; 251/88; 251/104; 251/107; 251/213; 251/349; 73/863.85; 73/863.86; 73/863.73

[58] Field of Search .......... 422/100, 102, 103, 104; 251/103, 104, 107, 349, 95, 88, 304, 213; 73/863.73, 863.85, 863.86, 863.87, 863.83, 863.84; 383/44

[56] References Cited

U.S. PATENT DOCUMENTS 789,795 5/1905 Chenery .......... 251/103
1,688,564 10/1928 Trinquart .......... 251/349
2,146,993 2/1939 Schroeder .......... 221/60
2,533,915 12/1950 Brooks .......... 222/513
3,047,239 7/1962 Canavan .......... 251/349
4,152,391 5/1979 Cabrera .......... 422/103
4,203,572 5/1980 Coffman .......... 251/95
4,557,377 12/1985 Maloney .......... 383/44
4,971,289 11/1990 Pietras .......... 251/95

FOREIGN PATENT DOCUMENTS 0381501 8/1990 European Pat. Off. .

*Primary Examiner*—James C. Housel
*Assistant Examiner*—Long V. Le
*Attorney, Agent, or Firm*—Dressler, Goldsmith, Shore, Sutker & Milnamow, Ltd.

[57] ABSTRACT

A lockable valve mechanism for introducing a liquid sample into an associated reaction vessel includes a valve body, and a valve member rotatably mounted thereon. The valve member is movable from an open position, wherein inlet and outlet passages of the valve mechanism are aligned for introduction of a sample into the reaction vessel, to a closed and sealed position, wherein the outlet passage of the valve body is sealed. The valve member includes a locking arrangement to prevent movement of the valve member out of the closed and sealed position after movement from the open position into the sealed position.

4 Claims, 3 Drawing Sheets

FIG. 1
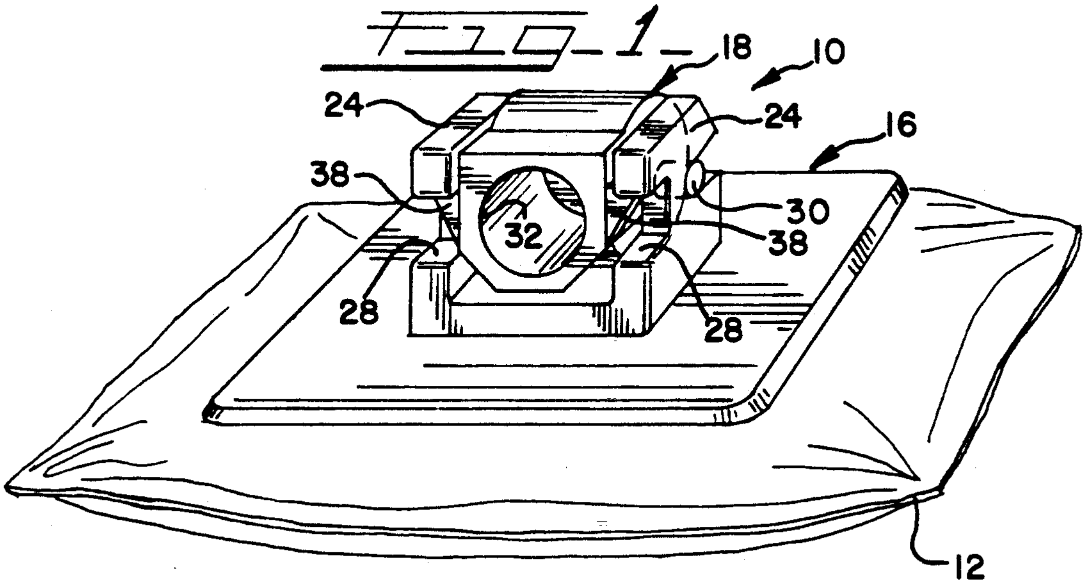
FIG. 2
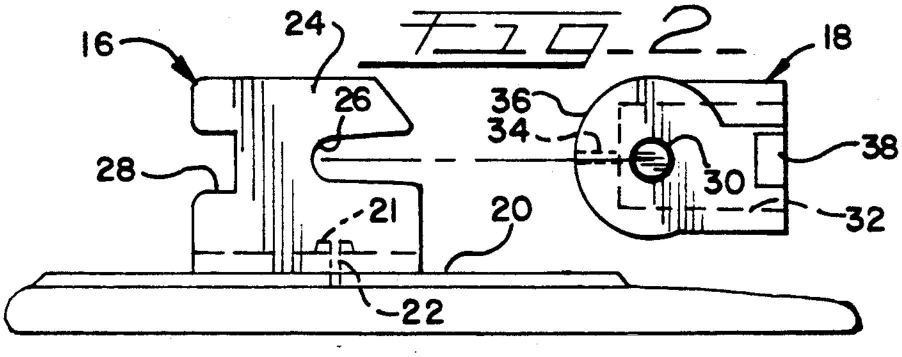
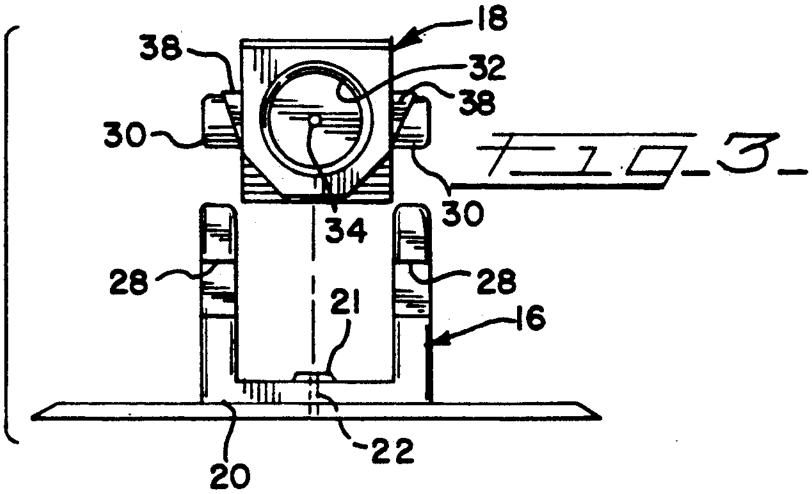
FIG. 3

LOCKABLE VALVE MECHANISM FOR SAMPLE POUCH

TECHNICAL FIELD

The present invention generally relates to devices for introducing a sample into a reaction vessel or like receptacle, and more particularly to a lockable valve mechanism which is movable from an open position to a sealed position, and automatically locked in the sealed position.

BACKGROUND OF THE INVENTION

Reaction vessels or receptacles comprising flexible pouches or blister-package constructions are frequently employed for performing chemical analyses or like test procedures. It is ordinarily necessary to provide an arrangement whereby one or more samples can be introduced into the reaction vessel to perform the required test protocol.

Reaction vessels of this type are frequently used to perform PCR (polymerase chain reaction) amplification, but such vessels must meet strict performance requirements. One of the most important of these requirements is that the vessel not leak during or after amplification. Examples of such vessels are shown in European Patent Application No. 381,501, designed to prevent leakage of amplified DNA which tends to release such DNA to the atmosphere where it can contaminate unused pouches and produce false positives.

Experience has shown that leakage is not a significant problem in pouches that are completely preassembled during manufacture. However, the sample to be amplified must be loaded into the pouch at the test facility. Ordinarily an access port is provided for this purpose, but the access port can act as a potential path for leakage after introduction of the sample.

The present invention contemplates a valve mechanism which can function as a loading port for a reaction vessel or like receptacle. The valve mechanism is configured to receive a sample from an associated pipette or like dispensing device, with the valve mechanism further being configured for closing and sealing, and automatic locking in the closed and sealed condition.

SUMMARY OF THE INVENTION

In accordance with the present invention, a lockable valve mechanism is disclosed for use with an associated reaction vessel or like receptacle, with the valve mechanism functioning as an entry port for introducing a sample or other fluid into the reaction vessel. Notably, the mechanism is configured such that it can be moved from an open position wherein the sample can be introduced into the vessel, to a closed and sealed position, with the mechanism including an automatic locking arrangement to prevent subsequent movement out of the closed and sealed position. Thus, leakage of the sample from within the vessel is substantially prevented.

In accordance with the illustrated embodiment, the present valve mechanism includes a valve body having a base portion for mounting the mechanism on the associated vessel. The valve body includes a pair of spaced apart side supports which extend upwardly from the base portion. The valve body defines a valve seat positioned between the side supports, and further defines an outlet passage extending through the valve seat for communication with the interior of the associated vessel.

The mechanism further includes a valve member movably mounted on the valve body generally between the side supports thereof. The valve member defines a convex, arcuate sealing portion engageable with the valve seat of the valve body, and further defines an inlet passage which extends through the sealing portion for receiving the sample to be introduced into the reaction vessel.

For use, the movable valve member is rotated relative to the valve body from an initial shipping position into an open position. In the open position, the inlet passage defined by the valve member and the outlet passage defined by the valve body are in substantial alignment and in fluid communication with each other so that the sample to be introduced can flow through the passages and into the associated vessel. In the preferred form, the valve member is configured to receive the sample from a pipette or like dispensing device.

After introduction of the sample into the reaction vessel, the valve member is movable from the open position to a sealed position, wherein the inlet and outlet passages are moved out of alignment, and the valve member seals the outlet passage of the valve body. In order to prevent inadvertent movement of the valve member back to the open position, the valve member includes a locking arrangement for automatically locking the valve member in the sealed position after movement thereto from the open position. In the illustrated embodiment, the locking arrangement comprises a pair of locking tabs defined by the valve member. When the valve member is moved into the sealed position, the locking tabs are respectively received in a pair of locking openings defined by the valve body.

To enhance the sealing engagement between the valve body and the valve member in the sealed position thereof, the present construction preferably includes an arrangement for urging the valve member into such sealing engagement as the valve member is moved from its open position into the sealed position. To this end, the valve member is rotatable relative to the valve body on a pair of support pins which define an axis of rotation positioned in eccentric relationship relative to the convex arcuate sealing portion of the valve member. Thus, as the valve member is rotated from its open position to its sealed position, its exterior sealing surface is urged against and into sealing engagement with the valve seat of the valve body, thus providing the desired enhanced sealing of the outlet passage defined by the valve body.

Other features and advantages of the present invention will become readily apparent from the following detailed description, the accompanying drawings, and the appended claims.

BRIEF DESCRIPTION OF THE DRAWINGS

FIG. 1 is a perspective view of a lockable valve mechanism embodying the principles of the present invention mounted on an associated reaction vessel;

FIG. 2 is an exploded side elevational view of the present valve mechanism;

FIG. 3 is an exploded end elevational view of the present valve mechanism;

DETAILED DESCRIPTION

Figures 4, 5, 6:
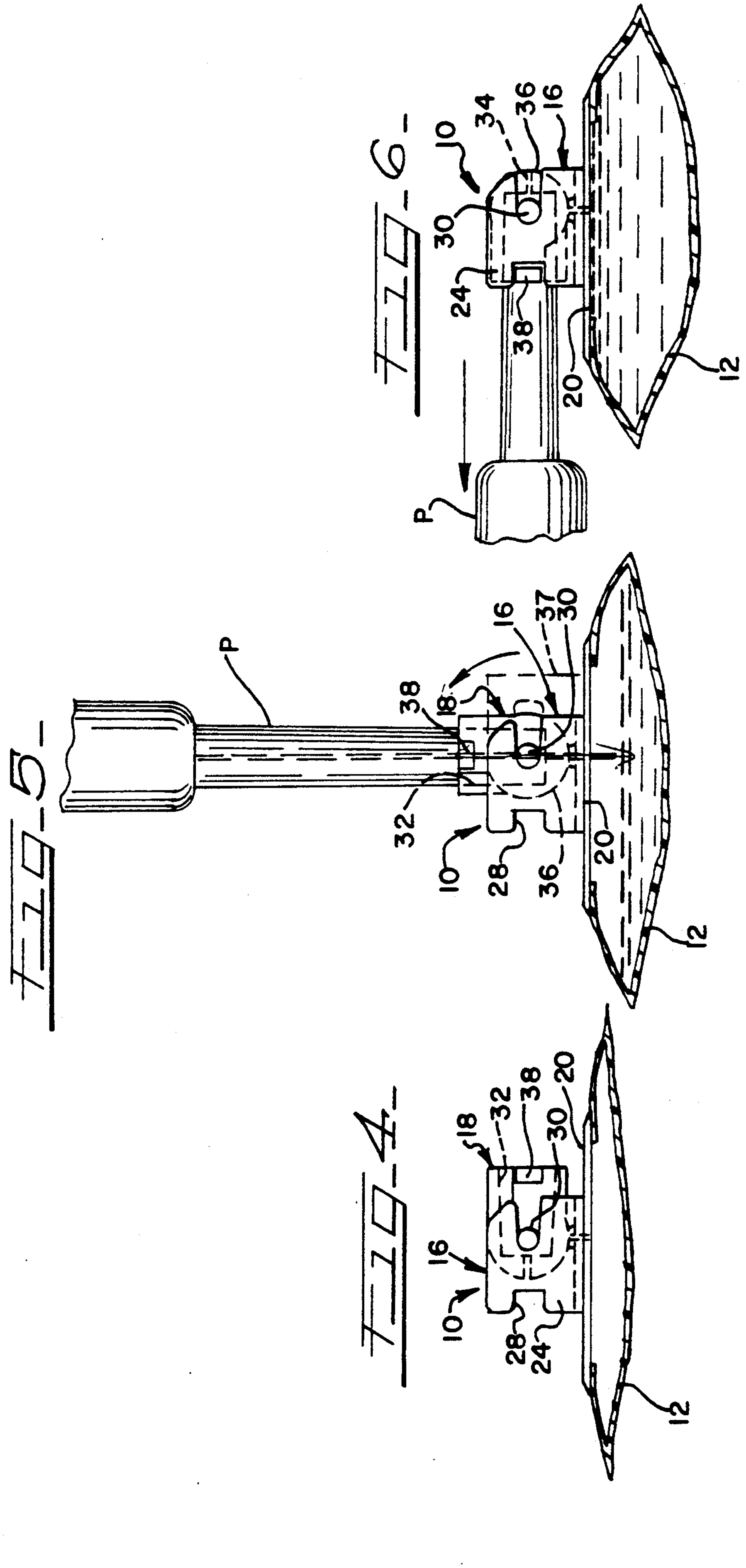
FIG. 4 is a side elevational view of the present valve mechanism illustrated in an initial, shipping position.
FIG. 5 is a view similar to FIG. 4 illustrating the present valve mechanism in an open position.
FIG. 6 is a view similar to FIG. 5 illustrating the present valve mechanism in a closed and sealed position.

While the present invention is susceptible of embodiment in various forms, there is shown in the drawings and will hereinafter be described a presently preferred embodiment, with the understanding that the present disclosure is to be considered as an exemplification of the invention, and is not intended to limit the invention to the specific embodiment illustrated.

With reference now to the drawings, therein is illustrated a lockable valve mechanism 10 embodying the principles of the present invention. By virtue of its ease of operation, positive sealing, and lockable nature, the present valve mechanism is particularly suitable for introduction of a liquid sample into an associated reaction vessel 12, such as for chemical analysis or the like. However, a valve mechanism embodying the principles disclosed herein can readily be configured for other applications.

As illustrated, reaction vessel 12 is illustrated in a typical pouch-like form, in the nature of a blister-package. Suitable heat seals or the like sealingly mount the valve mechanism 10 on the reaction vessel 12 with the valve mechanism functioning as an entry port for introduction of samples into the vessel.

The valve mechanism is desirably straightforward in construction for economical manufacture, and includes only two components which cooperate to provide the desired function. Specifically, the mechanism includes a valve body 16 mounted on the associated reaction vessel, and a valve member 18 rotatably movably mounted on the valve body, preferably by the provision of a snap-fit construction.

With particular reference to FIGS. 2 and 3, the valve body includes a base portion 20 configured for mounting on the associated reaction vessel. The base portion defines a generally centrally disposed valve seat 21 through which extends an outlet passage 22 for communication with the interior of the reaction vessel 12.

The valve body further defines a pair of upstanding, spaced-apart side supports 24 which extend generally upwardly from the base portion 20. In the preferred form, the side supports 24 respectively define a pair of support sockets 26 for receiving and rotatably mounting the associated valve member 18. Each of the support sockets 26 is preferably configured generally in the form of a converging recess which terminates in a circular opening, with the valve member being rotatably mounted in the pair of circular openings by a snap-fit.

The present valve mechanism is particularly configured for automatic locking when the mechanism is operated from its open to sealed positions. To this end, each of the side supports 24 defines a locking opening 28 which, as will be further described, cooperates with the valve member 18 for securely locking the valve member in its sealed position.

With further reference to FIGS. 2 and 3, the valve member 18 is positionable generally between the side supports 24 by respective snap-fit disposition of support pins 30 of the valve member within the support sockets 26. The valve member defines a pipette cavity 32 for receiving the tip of an associated dispensing pipette P.

A liquid sample from the pipette P flows through an inlet passage 34 defined by the valve member, with the inlet passage extending through an exterior, convex arcuate sealing portion 36 of the valve member. With the support pins 30 disposed in the support sockets 26, the arcuate sealing surface of the valve member cooperates with the valve seat of the valve body in the nature of a ball valve, whereby the inlet passage 34 and outlet passage 22 can be moved into and out of alignment and fluid communication with each other.

As will be further described, the valve member is movable from an initial shipping position, shown in FIG. 4, to an intermediate, open position (FIG. 5), and thereafter into a closed and locked sealed position, as shown in FIG. 6. Since it is desirable for the sealing portion 36 of the valve member to be firmly seated against the valve seat in the final closed position, the present valve mechanism is configured so as to urge the valve member into sealing engagement with the valve seat of the valve body as the valve member is moved from its open position to its closed position. Specifically, the support pins 30 defined by the valve member are positioned in eccentric relationship relative to the arcuate sealing portion 36 of the valve member. In the illustrated embodiment, this eccentric positioning results in the axis of rotation, defined by the support pins, being spaced a relatively greater distance from the sealing portion 34 which engages the valve seat in the closed position, as compared to the region of the sealing portion through which inlet passage 34 extends.

The lockable nature of the present valve mechanism is achieved by providing a pair of wedge-like locking tabs 38 generally on respective opposite sides of the valve member 18. The locking tabs 38 function in the manner of detents, and are respectively received within locking openings 28 when the valve member 18 is fully moved into its closed position. Thereafter, the locking tabs prevent movement of the valve member out of the closed and sealed position, thus assuring the sealing integrity of the valve mechanism.

Alternatively, valve body 16 can be extended to the shape shown in phantom, FIG. 5, to create a closed sidewall 37. Inside this sidewall a wad of absorbant can be optionally included, to catch and hold liquid leaking from passage 34.

From the foregoing description, the operation of the present valve mechanism will be readily apparent. As noted, the valve mechanism is preferably positioned as shown in FIG. 4 prior to use. For use, the valve member 18 is moved into the open position shown in FIG. 5, either by manipulation of the valve member, or by insertion of a pipette into the pipette cavity 32, with the pipette thereafter functioning as a lever to rotate the valve member.

With the valve member in the open position shown in FIG. 5, the liquid sample to be introduced into the reaction vessel is dispensed from the pipette, whereupon the sample flows through inlet passage 34, outlet passage 22, and into the vessel.

Upon completion of introduction of the sample, the pipette is employed as a lever for further rotating the valve member 18 from its open position, into its closed and sealed position, as shown in FIG. 6. Upon such movement, the eccentric positioning of support pins 30 acts in cooperation with the arcuate sealing portion 36 of the valve member to urge the sealing portion into sealing engagement with the valve seat 21. As the valve member is moved to its fully sealed position, locking tabs 38 are respectively received within the locking openings 28, with the locking tabs cooperating in a cam-like manner with the side supports 24 as the locking tabs move into the locking openings. Thereafter, the configuration of the locking tabs prevents movement of the valve member out of its closed and sealed position. The pipette is thereafter removed from the cavity 32, and introduction of the liquid sample into the reaction vessel complete.

Figure 7:
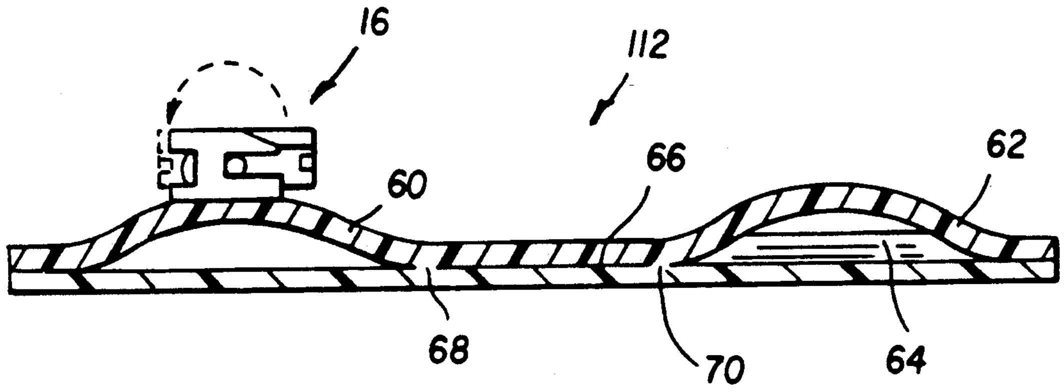
FIG. 7 is an elevational view similar to that of FIG. 4, but illustrating the invention in use in a multi-chambered vessel.

FIG. 7 illustrates the invention's use in a multi-chambered vessel 112. That is, the chamber 60 receiving the patient sample is not the only chamber, since chamber 62 is provided also with pre-incorporated reagent 64 therein. The two chambers are connected via a passageway 66, which has a temporary seal at 68 and 70, blocking premature flow of liquid between the chambers. Valve 16 is positioned and used as described above to fill chamber 60, and is then closed (the position shown in phantom). Any desired reaction is allowed to occur in chamber 60, after which external pressure is applied to break seals 68 and 70 and force liquid to flow from chamber 60 to 62 via passageway 66.

From the foregoing, it will be observed that numerous modifications and variations can be effected without departing from the true spirit and scope of the novel concept of the present invention. It is to be understood that no limitation with respect to the specific embodiment disclosed herein is intended or should be inferred. The disclosure is intended to cover, by the appended claims, all such modifications as fall within the scope of the claims.

What is claimed is:

1. A lockable valve mechanism for introducing a sample into an associated vessel, which comprises:

(a) a valve body including
  - a base portion which defines an aperture extending therethrough and has a smooth surface disposed transversely about the aperture forming a valve seat; and
  - a pair of spaced apart side supports composed of a resilient material, wherein said supports are attached to and extend away from said base portion, each support describes a circular opening and a locking opening, the supports are adapted to temporarily deform apart from an original spacing when subjected to an outwardly directed force but return substantially to the original spacing when the force subsides, and the circular openings are opposed and have centers on a line which is adjacent and substantially parallel to the valve seat; and (b) a valve member that defines a passage having a first end and a second end including
  - two circular support pins sharing a common axis, each pin protruding into one of the circular openings of the side supports, thereby mounting the valve member rotatably between the side supports, the common axis being positioned so that the first end of the passage is in alignment and communication with the aperture of the valve body when the valve member is rotated to an open position;
  - a smooth convex arcuate surface forming a first sealing portion which is positioned relative to the axis shared by the support pins so that the first sealing portion is in alignment and engaged in sealing contact with the valve seat when the valve member is rotated to a sealing position; and
  - outwardly beveled wedge-shaped locking tabs which have a width greater than the original spacing of the side supports and protrude into the locking openings of the side supports when the valve member is rotated to the sealing position, and which are adapted to move between and exert an outwardly directed force upon the side supports when the valve member is rotated to a position near the sealing position but exert relatively little outwardly directed force on the side supports when the valve member is in the sealing position, whereby rotation of the valve member toward the sealing position is facilitated but further rotation of the valve member after the locking tabs have entered the locking openings is hindered.

2. A lockable valve mechanism in accordance with claim 1 wherein said valve member includes a smooth arcuate surface forming a second sealing portion which is positioned relative to the axis shared by the support pins so that the second portion is in alignment and in sealing contact with the valve seat when the valve member is rotated to a shipping position.

3. A lockable valve mechanism in accordance with claim 1, wherein said first sealing portion of the valve member is in the shape of a portion of a cylinder having a longitudinal axis and said axis shared by the support pins is parallel to but spaced a distance from the longitudinal axis, whereby said sealing portion is urged against and into sealing engagement with said valve seat when said valve member is rotated from the open position to the sealing position.

4. A lockable valve mechanism in accordance with claim 1, wherein said second end of the passage defined by the valve member terminates in a pipette cavity, defined by the valve member, which is adapted to receive the tip of an associated dispensing pipette.

* * * * *